US010524737B2

(12) United States Patent
Sipolins et al.

(10) Patent No.: US 10,524,737 B2
(45) Date of Patent: Jan. 7, 2020

(54) CONDITION DETECTION IN A VIRTUAL REALITY SYSTEM OR AN AUGMENTED REALITY SYSTEM

(71) Applicant: International Business Machines Corporation, Armonk, NY (US)

(72) Inventors: Aldis Sipolins, New York City, NY (US); Jenna Reinen, Greenwich, CT (US); Hui Wu, White Plains, NY (US); Ravi Tejwani, Cambridge, MA (US); Marco Cavallo, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/974,178

(22) Filed: May 8, 2018

(65) Prior Publication Data

US 2019/0343465 A1 Nov. 14, 2019

(51) Int. Cl.
*A61B 5/00* (2006.01)
*G06F 3/01* (2006.01)
(Continued)

(52) U.S. Cl.
CPC .......... *A61B 5/7282* (2013.01); *A61B 5/0205* (2013.01); *A61B 5/0402* (2013.01); *A61B 5/1113* (2013.01); *A61B 5/1121* (2013.01); *A61B 5/4809* (2013.01); *A61B 5/7267* (2013.01); *A61B 5/747* (2013.01);
(Continued)

(58) Field of Classification Search
CPC combination set(s) only.
See application file for complete search history.

(56) References Cited

U.S. PATENT DOCUMENTS 6,201,476 B1 3/2001 Depeursinge et al.
6,433,690 B2 8/2002 Petelenz et al.
(Continued)

FOREIGN PATENT DOCUMENTS

WO 2010150260 A1 12/2010

OTHER PUBLICATIONS

Stokes, et al., "The Neuromuscular Origins of Kinematic Variability during Perturbed Walking," https://www.nature.com/articles/s41598-017-00942-x, Retrieved: Mar. 21, 2018, 26 pages.
(Continued)

*Primary Examiner* — Travis R Hunnings
(74) *Attorney, Agent, or Firm* — Amin, Turocy & Watson, LLP

(57) ABSTRACT

Techniques that facilitate condition detection in a virtual reality system and/or an augmented reality system are provided. In one example, a system includes a virtual reality component and an anomaly detection component. The virtual reality component collects motion data and biometric data from a virtual reality device. The motion data is indicative of motion information associated with one or more accelerometer sensors of the virtual reality device. The biometric data is indicative of biometric information associated with one or more biometric sensors of the virtual reality device. The anomaly detection component integrates the motion data and the biometric data into a machine learning model to generate anomaly detection data for the virtual reality device.

17 Claims, 10 Drawing Sheets

(51) Int. Cl.
  *A61B 5/0205* (2006.01)
  *A61B 5/0402* (2006.01)
  *A61B 5/11* (2006.01)
  *G06N 20/00* (2019.01)

(52) U.S. Cl.
  CPC .......... *A61B 5/7435* (2013.01); *A61B 5/7475* (2013.01); *G06F 3/011* (2013.01); *G06N 20/00* (2019.01); *A61B 2503/12* (2013.01); *A61B 2562/0219* (2013.01)

(56) References Cited

U.S. PATENT DOCUMENTS

| | | | |
|---|---|---|---|
| 8,206,325 | B1 | 6/2012 | Najafi et al. |
| 9,753,285 | B2 | 9/2017 | Imoto et al. |
| 2009/0048540 | A1 | 2/2009 | Otto et al. |
| 2011/0162433 | A1 | 7/2011 | Peng et al. |
| 2012/0101411 | A1 | 4/2012 | Hausdorff et al. |
| 2013/0054180 | A1 | 2/2013 | Barfield |
| 2014/0276130 | A1* | 9/2014 | Mirelman .............. A61B 5/744 600/483 |
| 2016/0054977 | A1 | 2/2016 | Gritton et al. |
| 2016/0370271 | A1 | 12/2016 | Kim et al. |
| 2017/0095732 | A1 | 4/2017 | Ghaffari et al. |

OTHER PUBLICATIONS

Dau, et al., "Phone based Fall Detection by Genetic Programming," Last Accessed: Mar. 21, 2018, 2 pages.
Derewicz, "Virtual reality could detect fall risk in seniors," http://www.futurity.org/virtual-reality-falls-elderly-1407522/, Apr. 20, 2017, 6 pages.
Diep, et al., "A Classifier Based Approach to Real-Time Fall Detection Using Low Cost Wearable Sensors," Last Accessed: Mar. 21, 2018, 7 pages.
Anonymous, "Virtual Reality headset with sensor for collision detection," Publication Date: Aug. 24, 2016, 5 pages.
Leone, et al., "Supervised Machine Learning Scheme for Tri-axial Accelerometer-based Fall Detector," 2013 IEEE, 4 pages.
Mehner, et al., "Location-independent Fall Detection with Smartphone," Last Accessed: Mar. 21, 2018, 8 pages.
Ojetola, et al., "Data Set for Fall Events and Daily Activities from Inertial Sensors," Last Accessed: Mar. 21, 2018, 6 pages.
Zhen, et al., "Wearable Preimpact Fall Detector using SVM," 2016 Tenth International Conference on Sensing Technology, 6 pages.

* cited by examiner

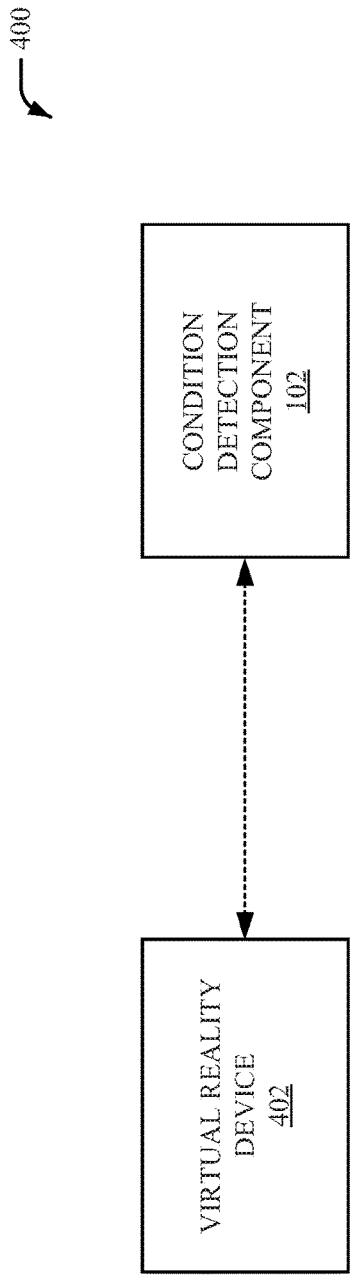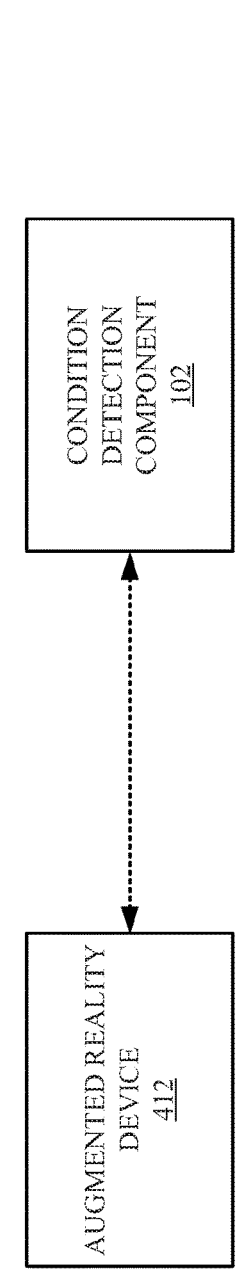

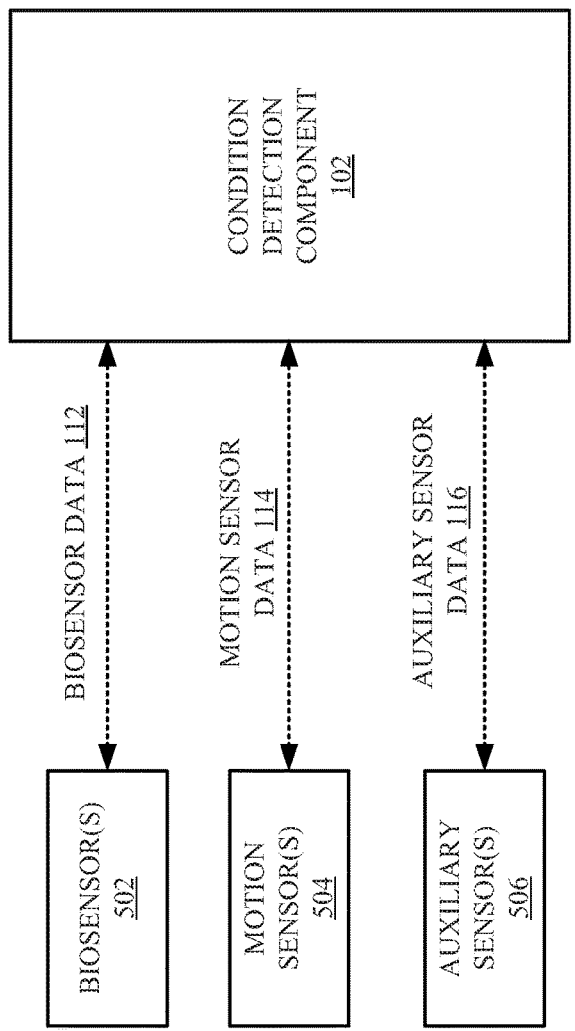

CONDITION DETECTION IN A VIRTUAL REALITY SYSTEM OR AN AUGMENTED REALITY SYSTEM

TECHNICAL FIELD

The subject disclosure relates to virtual reality systems and/or augmented reality systems.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate condition detection in a virtual reality system and/or an augmented reality system are described.

According to an embodiment, a system can comprise a virtual reality component and an anomaly detection component. The virtual reality component can collect motion data and biometric data from a virtual reality device. The motion data can be indicative of motion information associated with one or more accelerometer sensors of the virtual reality device. The biometric data can be indicative of biometric information associated with one or more biometric sensors of the virtual reality device. The anomaly detection component can integrate the motion data and the biometric data into a machine learning model to generate anomaly detection data for the virtual reality device.

According to another embodiment, a computer-implemented method is provided. The computer-implemented method can comprise collecting, by a system operatively coupled to a processor, motion data indicative of motion information associated with one or more motion sensors of a virtual reality device. The computer-implemented method can also comprise collecting, by the system, biometric data indicative of biometric information associated with one or more biometric sensors of a virtual reality device. Furthermore, the computer-implemented method can comprise generating, by the system, a machine learning model based on the motion data and the biometric data. The computer-implemented method can also comprise detecting, by the system, a condition for a user identity associated with the virtual reality device based on the machine learning model.

According to yet another embodiment, a computer program product for facilitating fall detection associated with virtual reality can comprise a computer readable storage medium having program instructions embodied therewith. The program instructions can be executable by a processor and cause the processor to obtain, by the processor, motion data indicative of motion information associated with one or more accelerometer sensors of a virtual reality device. The program instructions can also cause the processor to obtain, by the processor, biometric data indicative of biometric information associated with one or more biometric sensors of a virtual reality device. Furthermore, the program instructions can cause the processor to generate, by the processor, a machine learning model based on the motion data and the biometric data. The program instructions can also cause the processor to detect, by the processor, a condition for a user identity associated with the virtual reality device based on the machine learning model.

According to yet another embodiment, a system can comprise an information component, a similarity component and an analysis component. The information component can generate a first entropy measure for a first graph-structured dataset and a second entropy measure for a second graph-structured dataset. The similarity component can determine similarity between the first graph-structured dataset and the second graph-structured dataset based on a graph similarity computation associated with the first entropy measure and the second entropy measure. The analysis component can perform data analysis associated with the first graph-structured dataset and the second graph-structured dataset based on the graph similarity computation.

According to yet another embodiment, a computer-implemented method is provided. The computer-implemented method can comprise generating, by a system operatively coupled to a processor, a set of information indexes indicative of a set of entropy measures associated with a set of sequential changes for a set of graph data structures. The computer-implemented method can also comprise determining, by the system, similarity between the set of graph data structures based on a graph similarity computation associated with the set of information indexes. Furthermore, the computer-implemented method can comprise performing, by the system, a machine learning process based on the similarity between the set of graph data structures.

DESCRIPTION OF THE DRAWINGS

FIG. 4A illustrates a block diagram of an example, non-limiting system that includes a virtual reality device and a condition detection component in accordance with one or more embodiments described herein.

FIG. 4B illustrates a block diagram of an example, non-limiting system that includes an augmented reality device and a condition detection component in accordance with one or more embodiments described herein.

FIG. 5 illustrates an example, non-limiting system that includes biosensors, motion sensors and/or auxiliary sensors associated with a condition detection component in accordance with one or more embodiments described herein.

DETAILED DESCRIPTION

Figure 1:
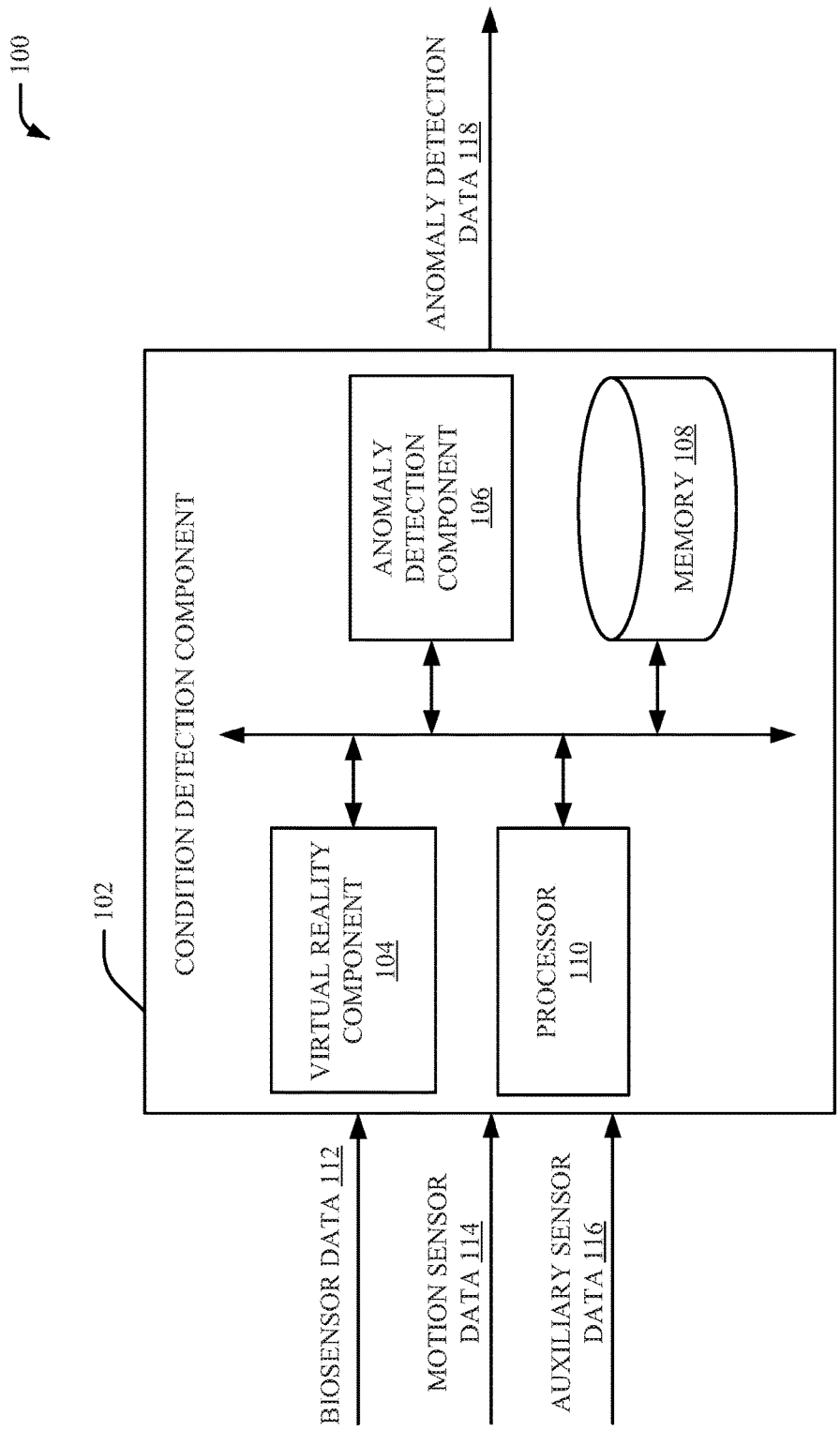
FIG. 1 illustrates a block diagram of an example, non-limiting system that includes a condition detection component in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Virtual reality is a computer-generated environment that is generally simulated via a virtual reality device. Augmented reality employs a real-world environment to insert augmented elements that are computer-generated into the real-world environment. Due to the immersive nature of virtual reality and/or augmented reality, there is an increased risk of injury for a user that employs a virtual reality device and/or a computing device associated with augmented reality. For example, a user that employs a virtual reality device and/or a computing device associated with augmented reality generally has in increased risk for running into an object (e.g., running into a wall), an increased risk for hitting an object with the virtual reality device or the computing device, etc. However, conventional virtual reality systems and/or conventional augmented reality systems cannot determine when a user is associated with a condition associated with an injury. Furthermore, with conventional virtual reality systems and/or conventional augmented reality systems, there is generally an increased risk of damaging a virtual reality device and/or a computing device associated with augmented reality.

To address these and/or other issues, embodiments described herein include systems, computer-implemented methods, and computer program products that facilitate condition detection in a virtual reality system and/or an augmented reality system. For instance, fall detection for a user associated with a virtual reality system and/or an augmented reality system can be realized. In an embodiment, machine learning can be employed to detect when a condition for a user identity associated with a virtual reality system and/or an augmented reality system has occurred. In an aspect, motion sensor data, biosensor data and/or auxiliary sensor data can be employed by machine learning to detect when a condition for a user identity associated with a virtual reality system and/or an augmented reality system has occurred. The motion sensor data can be obtained from one or more motion sensors and/or one or more rotational sensors. For example, the motion sensor data can be obtained from one or more accelerometers, one or more gyroscopes, one more other motion sensors, and/or one or more other rotational sensors. The motion sensor data can include, for example, rotational data and/or positional data for a virtual reality device, a computing device associated with augmented reality, and/or a motion controller. The biosensor data can be obtained from one or more biosensors that record bio-activity associated with a virtual reality system and/or an augmented reality system. In one example, the biosensor data can be obtained from one or more electrocardiography sensors. The auxiliary sensor data can be obtained from one or more auxiliary sensors. For example, the auxiliary sensor data can be obtained from one or more cameras, one or more microphones and/or one or more other sensors external from a virtual reality device and/or a computing device associated with augmented reality. In another embodiment, a classification by the machine learning system for the condition (e.g., the condition for the user identity associated with the virtual reality system and/or the augmented reality system) can be reported to an external system or a network of computing devices. In one example, the external system can be a medical response system. In yet another embodiment, an alert can be presented on a display of the virtual reality device and/or the computing device associated with augmented reality based on the classification by the machine learning system for the condition (e.g., the condition for the user identity associated with the virtual reality system and/or the augmented reality system). As such, likelihood of a medical condition for a user identity associated with a virtual reality device and/or a computing device associated with augmented reality can be reduced. Furthermore, likelihood of damage to a virtual reality device and/or a computing device associated with augmented reality can be reduced. Moreover, accuracy of data generated by a machine learning process to facilitate condition detection in a virtual reality system and/or an augmented reality system can be improved. Quality of a machine learning process to facilitate condition detection in a virtual reality system and/or an augmented reality system can also be improved.

FIG. 1 illustrates a block diagram of an example, non-limiting system 100 that facilitates condition detection in a virtual reality system and/or an augmented reality system in accordance with one or more embodiments described herein. In various embodiments, the system 100 can be a condition detection system associated with technologies such as, but not limited to, virtual reality technologies, augmented reality technologies, machine learning technologies, artificial intelligence technologies, digital technologies, sensor technologies, data analysis technologies, data analytics technologies, cloud computing technologies, computer technologies, server technologies, and/or other technologies. The system 100 can employ hardware and/or software to solve problems that are highly technical in nature, that are not abstract and that cannot be performed as a set of mental acts by a human. Further, some of the processes performed may be performed by one or more specialized computers (e.g., one or more specialized processing units, a specialized computer with a condition detection component, etc.) for carrying out defined tasks related to condition detection and/or machine learning associated with a virtual reality system and/or an augmented reality system. The system 100 and/or components of the system can be employed to solve new problems that arise through advancements in technologies mentioned above, employment of virtual reality systems, employment of augmented reality systems, and/or computer architecture, and the like. One or more embodiments of the system 100 can provide technical improvements to a system associated with technologies such as, but not limited to, virtual reality systems, augmented reality systems, machine learning systems, artificial intelligence systems, digital systems, sensor systems, data analysis systems, data analytics systems, cloud computing systems, computer systems, server systems, and/or other systems.

In the embodiment shown in FIG. 1, the system 100 can include a condition detection component 102. As shown in FIG. 1, the condition detection component 102 can include a virtual reality component 104 and an anomaly detection component 106. Aspects of the condition detection component 102 can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. In an aspect, the condition detection component 102 can also include memory 108 that stores computer executable components and instructions. Furthermore, the condition detection component 102 can include a processor 110 to facilitate execution of the instructions (e.g., computer executable components and corresponding instructions) by the condition detection component 102. As shown, the virtual reality component 104, the anomaly detection component 106, the memory 108 and/or the processor 110 can be electrically and/or communicatively coupled to one another in one or more embodiments. In certain embodiments, the condition detection component 102 can be in communication with a virtual reality system and/or an augmented reality system.

The condition detection component 102 (e.g., the virtual reality component 104 of the condition detection component 102) can receive biosensor data 112, motion sensor data 114, and/or auxiliary sensor data 116. For instance, the virtual reality component 104 can collect the biosensor data 112, the motion sensor data 114, and/or the auxiliary sensor data 116 from a virtual reality device and/or a computing device associated with augmented reality. The biosensor data 112 can be biometric data received from one or more biosensors. In one embodiment, the one or more biosensors can be one or more biosensors of a virtual reality device. The virtual reality device can provide a virtual reality environment to a user that employs the virtual reality deice. In one example, the virtual reality device can be a virtual reality headset (e.g., a head-mounted device) with a display that provides a virtual reality environment to a user that wears the virtual reality headset. In another embodiment, the one or more biosensors can be one or more biosensors of a computing device associated with augmented reality. The computing device can be a smart phone, a mobile device, a handheld device, a tablet, a wearable device, a smart device, a portable computing device, a computer, a desktop computer, a laptop computer, a monitor device, or another type of device associated with a display. In an aspect, the computing device can render a real-world environment on a display of the computing device and the computing device can insert one or more augmented elements that are computer-generated into the real-world environment to generate an augmented reality environment. Furthermore, the one or more biosensors can record bio-activity associated with a virtual reality system and/or an augmented reality system. In certain embodiments, the one or more biosensors can be one or more electrocardiography sensors that obtain electrical activity of a biological heart during a period of time. For instance, the biosensor data 112 can be obtained from one or more electrocardiography sensors.

The motion sensor data 114 can be motion data received from one or more motion sensors. In one example, the one or more motion sensors can include one or more rotational sensors. For instance, the motion sensor data 114 can be rotational data received from one or more rotational sensors. Additionally or alternatively, the one or more motion sensors can include one or more positional sensors. For instance, the motion sensor data 114 can be positional data received from one or more positional sensors. In certain embodiments, the one or more motion sensors can be one or more accelerometers and/or one or more gyroscopes. For example, the motion sensor data 114 can include rotational data indicative of rotational information associated with one or more accelerometer sensors and/or positional data indicative of positional information associated with one or more positional sensors. In one embodiment, the one or more motion sensors can be one or more motion sensors of the virtual reality device. In another embodiment, the one or more motion sensors can be one or more motion sensors of the computing device associated with augmented reality. In yet another embodiment, the one or more motion sensors can be one or more motion sensors of a motion controller.

The auxiliary sensor data 116 can be auxiliary data received from one or more auxiliary sensors. In one embodiment, the one or more auxiliary sensors can be one or more sensors external from the virtual reality device. In one example, the one or more auxiliary sensors can be one or more cameras, one or more microphones and/or one or more other sensors external from the virtual reality device. For instance, the auxiliary sensor data 116 can include optical data indicative of optical information associated with one or more auxiliary sensors external from the virtual reality device (e.g., one or more cameras, one or more microphones and/or one or more other sensors external from the virtual reality device). Additionally or alternatively, the auxiliary sensor data 116 can include auditory data indicative of auditory information associated with one or more auxiliary sensors external from the virtual reality device (e.g., one or more cameras, one or more microphones and/or one or more other sensors external from the virtual reality device). In another embodiment, the one or more auxiliary sensors can be one or more sensors external from the computing device associated with augmented reality. In one example, the one or more auxiliary sensors can be one or more cameras, one or more microphones and/or one or more other sensors external from the computing device associated with augmented reality. For instance, the auxiliary sensor data 116 can include optical data indicative of optical information associated with one or more auxiliary sensors external from the computing device associated with augmented reality (e.g., one or more cameras, one or more microphones and/or one or more other sensors external from the computing device associated with augmented reality). Additionally or alternatively, the auxiliary sensor data 116 can include auditory data indicative of auditory information associated with one or more auxiliary sensors external from the computing device associated with augmented reality (e.g., one or more cameras, one or more microphones and/or one or more other sensors external from the computing device associated with augmented reality).

The anomaly detection component 106 can integrate the biosensor data 112, the motion sensor data 114 and/or the auxiliary sensor data 116 into a machine learning model to generate anomaly detection data 118. For instance, the anomaly detection component 106 can integrate the biosensor data 112, the motion sensor data 114 and/or the auxiliary sensor data 116 into the machine learning model to generate anomaly detection data 118 for the virtual reality device. Alternatively, the anomaly detection component 106 can integrate the biosensor data 112, the motion sensor data 114 and/or the auxiliary sensor data 116 into the machine learning model to generate anomaly detection data 118 for the computing device associated with augmented reality. For instance, the machine learning model can determine whether a classifiable pattern is associated with the biosensor data 112, the motion sensor data 114 and/or the auxiliary sensor data 116 to determine whether a condition for a user of a virtual reality device and/or a computing device exists. For example, the machine learning model can detect rapid deceleration of a virtual reality device and/or a computing device associated with augmented reality. In another example, the machine learning model can detect rapid deceleration of a motion controller associated with a virtual reality device and/or a computing device associated with augmented reality. In yet another example, the machine learning model can detect a slower heartrate of a user and a slower breathing rate of the user after a fall. In an aspect, the machine learning model can be a classifier that provides a confidence score for a condition (e.g., a fall condition) associated with a user. In certain embodiments, the machine learning model can be associated with a shallow classifier such as, for example, a support vector machine, a random forest, etc. In certain embodiments, the machine learning model can be associated with a deep neural network. However, it is to be appreciated that the machine learning model can be associated with another type of machine learning technique and/or another type of artificial intelligence technique.

In an embodiment, the anomaly detection component 106 can determine whether the anomaly detection data 118 satisfies a defined criterion associated with a medical event for a user identity associated with the virtual reality device. For example, the anomaly detection component 106 can determine whether the anomaly detection data 118 satisfies a defined criterion associated with a concussion medical status for a user identity associated with the virtual reality device. In another example, the anomaly detection component 106 can determine a period of unconsciousness for a user identity associated with the virtual reality device based on the anomaly detection data 118. In certain embodiments, the anomaly detection component 106 can transmit a message to a medical emergency device in response to a determination that the anomaly detection data 118 satisfies a defined criterion associated with a medical event for the user identity associated with the virtual reality device. In certain embodiments, the anomaly detection component 106 can generate a graphical user interface for the virtual reality device in response to a determination that the anomaly detection data 118 satisfies a defined criterion associated with a medical event for the user identity associated with the virtual reality device. In an aspect, the anomaly detection component 106 can transmit a message to a medical emergency device in response to a determination that the graphical user interface satisfies another defined criterion associated with the user identity. In another aspect, the anomaly detection component 106 can generate the anomaly detection data 118 for the virtual reality device to facilitate reduced likelihood of a medical condition for the user identity associated with the virtual reality device.

In another embodiment, the anomaly detection component 106 can determine whether the anomaly detection data 118 satisfies a defined criterion associated with a medical event for a user identity associated with the computing device associated with augmented reality. For example, the anomaly detection component 106 can determine whether the anomaly detection data 118 satisfies a defined criterion associated with a concussion medical status for a user identity associated with the computing device associated with augmented reality. In another example, the anomaly detection component 106 can determine a period of unconsciousness for a user identity associated with the computing device associated with augmented reality based on the anomaly detection data 118. In certain embodiments, the anomaly detection component 106 can transmit a message to a medical emergency device in response to a determination that the anomaly detection data 118 satisfies a defined criterion associated with a medical event for the user identity associated with the computing device associated with augmented reality. In certain embodiments, the anomaly detection component 106 can generate a graphical user interface for the computing device associated with augmented reality in response to a determination that the anomaly detection data 118 satisfies a defined criterion associated with a medical event for the user identity associated with the computing device associated with augmented reality. In an aspect, the anomaly detection component 106 can transmit a message to a medical emergency device in response to a determination that the graphical user interface satisfies another defined criterion associated with the user identity. In another aspect, the anomaly detection component 106 can generate the anomaly detection data 118 for the computing device associated with augmented reality to facilitate reduced likelihood of a medical condition for the user identity associated with the computing device associated with augmented reality.

It is to be appreciated that the condition detection component 102 (e.g., the virtual reality component 104 and/or the anomaly detection component 106) performs a condition detection process associated with virtual reality system and/or an augmented reality system that cannot be performed by a human (e.g., is greater than the capability of a single human mind). For example, an amount of data processed, a speed of processing of data (e.g., a speed of processing data associated with multiple parties) and/or data types processed by the condition detection component 102 (e.g., the virtual reality component 104 and/or the anomaly detection component 106) over a certain period of time can be greater, faster and different than an amount, speed and data type that can be processed by a single human mind over the same period of time. The condition detection component 102 (e.g., the virtual reality component 104 and/or the anomaly detection component 106) can also be fully operational towards performing one or more other functions (e.g., fully powered on, fully executed, etc.) while also performing the above-referenced condition detection process. Moreover, the condition detection component 102 (e.g., the virtual reality component 104 and/or the anomaly detection component 106) can determine information that is impossible to obtain manually by a user. For example, a type of information included in the anomaly detection data 118, timing for generating the anomaly detection data 118, an amount of information included in the anomaly detection data 118 and/or a variety of information included in the anomaly detection data 118 can be more complex than information obtained manually by a user.

Figure 2:
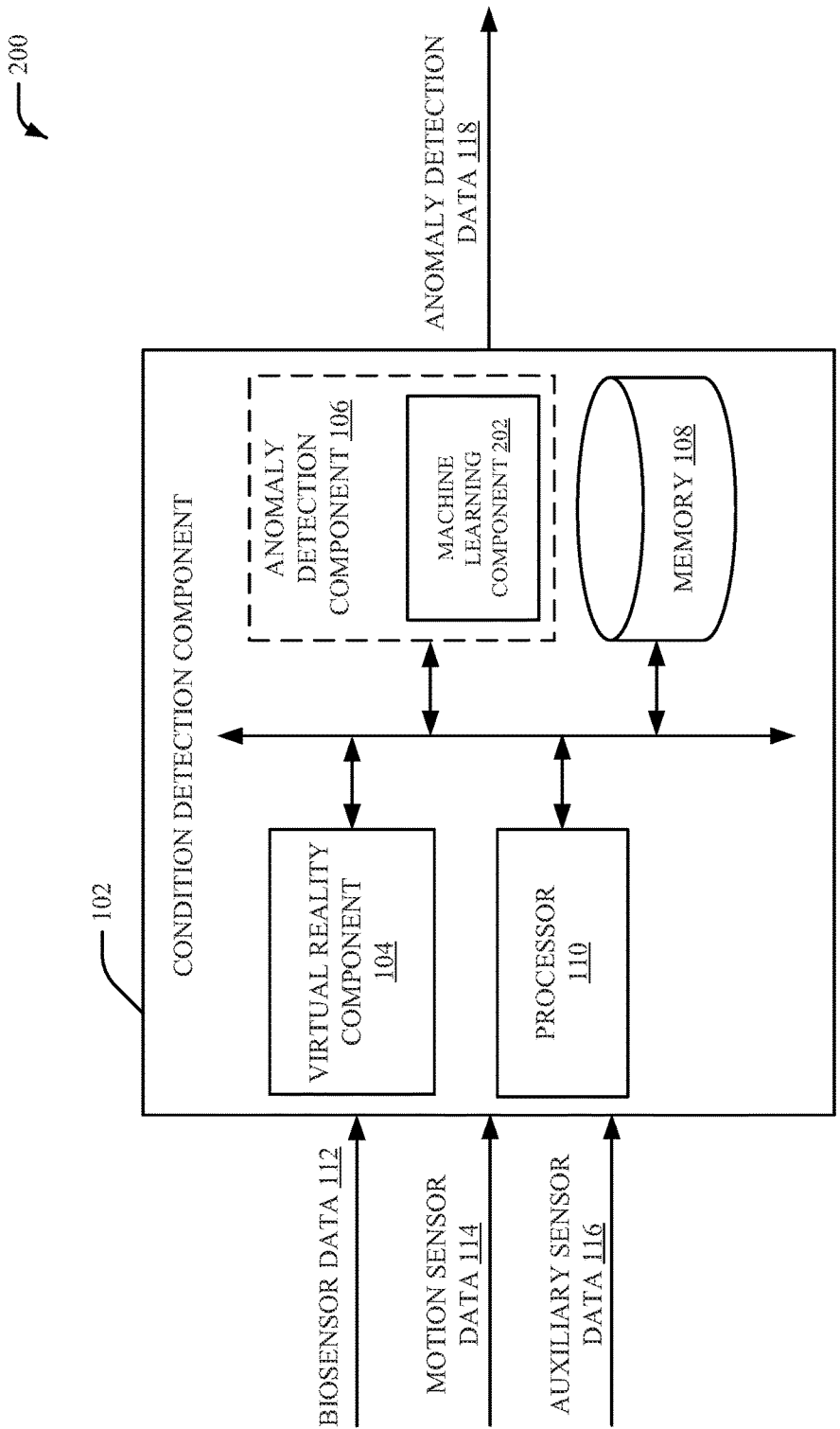
FIG. 2 illustrates a block diagram of another example, non-limiting system that includes a condition detection component in accordance with one or more embodiments described herein.

FIG. 2 illustrates a block diagram of an example, non-limiting system 200 in accordance with one or more embodiments described herein. Repetitive description of like elements employed in other embodiments described herein is omitted for sake of brevity.

The system 200 includes the condition detection component 102. The condition detection component 102 can include the virtual reality component 104, the anomaly detection component 106, the memory 108 and/or the processor 110. The anomaly detection component 106 can include a machine learning component 202. The machine learning component 202 can perform one or more machine learning processes to facilitate analysis of the biosensor data 112, the motion sensor data 114 and/or the auxiliary sensor data 116. In an embodiment, the machine learning component 202 can employ machine learning and/or principles of artificial intelligence (e.g., a machine learning process) to learn one or more patterns, one or more inferences, one or more correlations, one or more features and/or information related to the biosensor data 112, the motion sensor data 114 and/or the auxiliary sensor data 116. In an aspect, the machine learning component 202 can employ machine learning and/or principles of artificial intelligence (e.g., a machine learning process) to generate the anomaly detection data 118. The machine learning component 202 can perform learning with respect to learning one or more patterns, one or more inferences, one or more correlations, one or more features and/or information related to the biosensor data 112, the motion sensor data 114 and/or the auxiliary sensor data 116 explicitly or implicitly. In an aspect, the machine learning component 202 can learn one or more patterns, one or more inferences, one or more correlations, one or more features and/or information related to the biosensor data 112, the motion sensor data 114 and/or the auxiliary sensor data 116 based on classifications, correlations, inferences and/or expressions associated with principles of artificial intelligence. For instance, the machine learning component 202 can employ an automatic classification system and/or an automatic classification process to learn one or more patterns, one or more inferences, one or more correlations, one or more features and/or information related to the biosensor data 112, the motion sensor data 114 and/or the auxiliary sensor data 116. In one example, the machine learning component 202 can employ a probabilistic and/or statistical-based analysis (e.g., factoring into the analysis utilities and costs) to learn and/or generate inferences with respect to the biosensor data 112, the motion sensor data 114 and/or the auxiliary sensor data 116. In an aspect, the machine learning component 202 can include an inference component (not shown) that can further enhance automated aspects of the machine learning component 202 utilizing in part inference based schemes to learn one or more patterns, one or more inferences, one or more correlations, one or more features and/or information related to the biosensor data 112, the motion sensor data 114 and/or the auxiliary sensor data 116.

The machine learning component 202 can employ any suitable machine-learning based techniques, statistical-based techniques and/or probabilistic-based techniques. For example, the machine learning component 202 can employ expert systems, fuzzy logic, SVMs, Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, etc. In another aspect, the machine learning component 202 can perform a set of machine learning computations associated with learning one or more patterns, one or more inferences, one or more correlations, one or more features and/or information related to the biosensor data 112, the motion sensor data 114 and/or the auxiliary sensor data 116. For example, the machine learning component 202 can perform a set of clustering machine learning computations, a set of logistic regression machine learning computations, a set of decision tree machine learning computations, a set of random forest machine learning computations, a set of regression tree machine learning computations, a set of least square machine learning computations, a set of instance-based machine learning computations, a set of regression machine learning computations, a set of support vector regression machine learning computations, a set of k-means machine learning computations, a set of spectral clustering machine learning computations, a set of rule learning machine learning computations, a set of Bayesian machine learning computations, a set of deep Boltzmann machine computations, a set of deep belief network computations, and/or a set of different machine learning computations to learn one or more patterns, one or more inferences, one or more correlations, one or more features and/or information related to the biosensor data 112, the motion sensor data 114 and/or the auxiliary sensor data 116.

Figure 3:
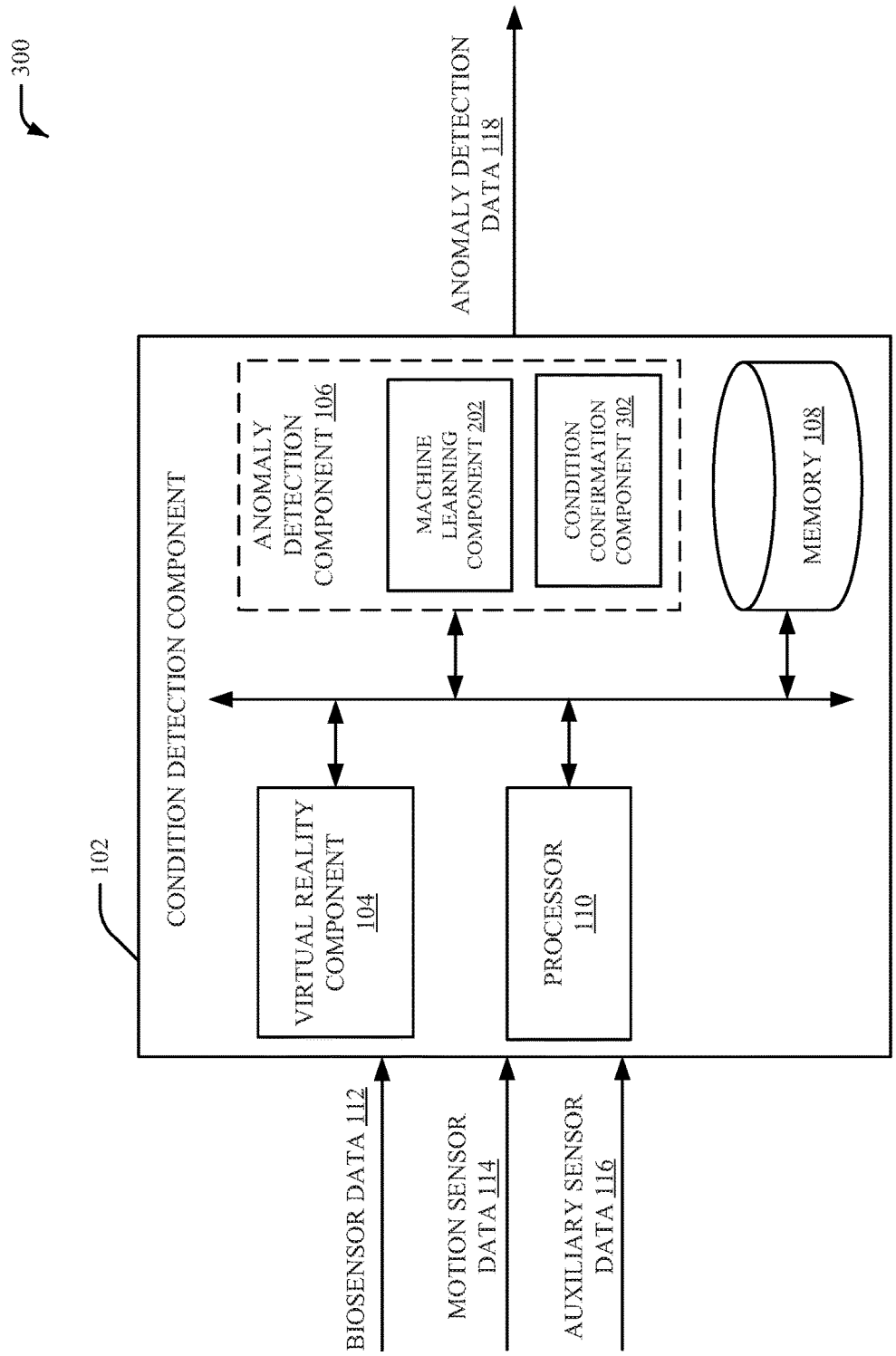
FIG. 3 illustrates a block diagram of yet another example, non-limiting system that includes a condition detection component in accordance with one or more embodiments described herein.

FIG. 3 illustrates a block diagram of an example, non-limiting system 300 in accordance with one or more embodiments described herein. Repetitive description of like elements employed in other embodiments described herein is omitted for sake of brevity.

The system 300 includes the condition detection component 102. The condition detection component 102 can include the virtual reality component 104, the anomaly detection component 106, the memory 108 and/or the processor 110. The anomaly detection component 106 can include the machine learning component 202 and/or a condition confirmation component 302. The condition confirmation component 302 can be employed to facilitate confirmation of a condition associated with user identity for a virtual reality system and/or an augmented reality system. For example, in response to a determination that the anomaly detection data 118 satisfies a defined criterion associated with a medical event for a user identity associated with the virtual reality device, the condition confirmation component 302 can generate a graphical user interface for a display of the virtual reality device. The graphical user interface generated by the condition confirmation component 302 can confirm, for example, that the user identity is associated with a medical event. For instance, the condition confirmation component 302 can present a message on the graphical user interface for the virtual reality device to ask a user to confirm that no medical attention is needed. In response to a determination that the message satisfies a defined criterion, the condition confirmation component 302 can transmit a message to a medical emergency system (e.g., a medical emergency device). For example, in response to a determination that no response is provided via the graphical user interface of the virtual reality device during a defined period of time that the message is displayed, the condition confirmation component 302 can transmit a message to a medical emergency system (e.g., a medical emergency device). In another example, in response to a determination that the anomaly detection data 118 satisfies a defined criterion associated with a medical event for a user identity associated with the computing device associated with augmented reality, the condition confirmation component 302 can generate a graphical user interface for a display of the computing device associated with augmented reality. The graphical user interface generated by the condition confirmation component 302 can confirm, for example, that the user identity is associated with a medical event. For instance, the condition confirmation component 302 can present a message on the graphical user interface for the computing device associated with augmented reality to ask a user to confirm that no medical attention is needed. In response to a determination that the message satisfies a defined criterion, the condition confirmation component 302 can transmit a message to a medical emergency system (e.g., a medical emergency device). For example, in response to a determination that no response is provided via the graphical user interface of the computing device associated with augmented reality during a defined period of time that the message is displayed, the condition confirmation component 302 can transmit a message to a medical emergency system (e.g., a medical emergency device).

FIG. 4A illustrates a block diagram of an example, non-limiting system 400 in accordance with one or more embodiments described herein. Repetitive description of like elements employed in other embodiments described herein is omitted for sake of brevity.

The system 400 includes a virtual reality device 402 and the condition detection component 102. The condition detection component 102 can include the virtual reality component 104, the anomaly detection component 106, the memory 108, the processor 110, the machine learning component 202 and/or the condition confirmation component 302. The virtual reality device 402 can be computing device with a head-mounted display to facilitate providing a virtual reality environment to a user (e.g., a user identity) that employs the virtual reality device 402. In one example, the virtual reality device 402 can be a virtual reality headset (e.g., a head-mounted device) with a display that provides a virtual reality environment to a user that wears the virtual reality headset. A display of the virtual reality device 402 can be, for example, stereoscopic head-mounted display that provides two offset images separately to a first eye and a second eye of the user. The two offset images can be two-dimensional images that can be combined to create a three-dimensional environment for the virtual reality environment. In an aspect, the virtual reality device 402 can include one or more gyroscopes, one or more accelerometers, and/or one or more other motions sensors. In an embodiment, the virtual reality device 402 can include the condition detection component 102. In another embodiment, the condition detection component 102 can be separate from the virtual reality device 402 and in communication with the virtual reality device 402. For example, the condition detection component 102 can be in communication with the virtual reality device 402 via a wireless network and/or a wired network associated with a wide area network (WAN, e.g., the Internet), a local area network (LAN), a cellular network, and/or communication network. In an aspect, the condition detection component 102 can monitor the virtual reality device 402. For instance, the condition detection component 102 can repeatedly obtain biosensor data (e.g., biosensor data 112), motion sensor data (e.g., motion sensor data 114) and/or auxiliary sensor data (e.g., auxiliary sensor data 116) from the virtual reality device 402 and/or a virtual reality system associated with the virtual reality device 402.

FIG. 4B illustrates a block diagram of an example, non-limiting system 410 in accordance with one or more embodiments described herein. Repetitive description of like elements employed in other embodiments described herein is omitted for sake of brevity.

The system 410 includes an augmented reality device 412 and the condition detection component 102. The condition detection component 102 can include the virtual reality component 104, the anomaly detection component 106, the memory 108, the processor 110, the machine learning component 202 and/or the condition confirmation component 302. The augmented reality device 412 can be computing device associated with augmented reality. For instance, the augmented reality device 412 can be a smart phone, a mobile device, a handheld device, a tablet, a wearable device, a smart device, a portable computing device, a computer, a desktop computer, a laptop computer, a monitor device, or another type of device associated with a display to facilitate augmented reality. In an aspect, the augmented reality device 412 can provide an augmented reality environment to a user (e.g., a user identity) that employs the augmented reality device 412. For example, the augmented reality device 412 can render a real-world environment on a display of the augmented reality device 412. Furthermore, the augmented reality device 412 can insert one or more augmented elements that are computer-generated into the real-world environment associated with the augmented reality device 412. In another aspect, the augmented reality device 412 can include one or more gyroscopes, one or more accelerometers, one or more other motions sensors, a global positioning system and/or a compass. In an embodiment, the augmented reality device 412 can include the condition detection component 102. In another embodiment, the condition detection component 102 can be separate from the augmented reality device 412 and in communication with the augmented reality device 412. For example, the condition detection component 102 can be in communication with the augmented reality device 412 via a wireless network and/or a wired network associated with a wide area network (WAN, e.g., the Internet), a local area network (LAN), a cellular network, and/or communication network. In an aspect, the condition detection component 102 can monitor the augmented reality device 412. For instance, the condition detection component 102 can repeatedly obtain biosensor data (e.g., biosensor data 112), motion sensor data (e.g., motion sensor data 114) and/or auxiliary sensor data (e.g., auxiliary sensor data 116) from the augmented reality device 412 and/or an augmented reality system associated with the augmented reality device 412.

FIG. 5 illustrates a block diagram of an example, non-limiting system 500 in accordance with one or more embodiments described herein. Repetitive description of like elements employed in other embodiments described herein is omitted for sake of brevity.

The system 500 includes one or more biosensors 502, one or more motion sensors 504 and/or one or more auxiliary sensors 506. The one or more biosensors 502 can provide, for example, the biosensor data 112 to the condition detection component 102. The condition detection component 102 can include the virtual reality component 104, the anomaly detection component 106, the memory 108, the processor 110, the machine learning component 202 and/or the condition confirmation component 302. In an embodiment, the one or more biosensors 502 can be one or more biosensors of a virtual reality device (e.g., the virtual reality device 402). In another embodiment, the one or more biosensors 502 can be one or more biosensors of a computing device associated with augmented reality (e.g., the augmented reality device 412). Furthermore, the one or more biosensors 502 can record bio-activity associated with the virtual reality device and/or the computing device associated with augmented reality. For example, the one or more biosensors 502 can record bio-activity associated with a user (e.g., a user identity) that employs the virtual reality device and/or the computing device associated with augmented reality. In certain embodiments, the one or more biosensors 502 can be one or more electrocardiography sensors that obtain electrical activity of a biological heart of the user (e.g., the user identity) during a period of time. In certain embodiments, the one or more biosensors 502 can be one or more heart rate sensors that calculate a heart rate for the user (e.g., the user identity) during a period of time. However, it is to be appreciated that the one or more biosensors 502 can include one or more different types of biosensors.

The one or more motion sensors 504 can additionally or alternatively provide, for example, the motion sensor data 114 to the condition detection component 102. In one example, the one or more motion sensors 504 can include one or more rotational sensors. For instance, the one or more motion sensors 504 can generate rotational data associated with the virtual reality device and/or the computing device associated with augmented reality. Additionally or alternatively, the one or more motion sensors 504 can include one or more positional sensors. For instance, the one or more motion sensors 504 can generate positional data associated with the virtual reality device and/or the computing device associated with augmented reality. In certain embodiments, the one or more motion sensors 504 can be one or more accelerometers and/or one or more gyroscopes. In certain embodiments, the one or more motion sensors 504 can be included in a motion controller for the virtual reality device and/or the computing device associated with augmented reality.

The one or more auxiliary sensors 506 can additionally or alternatively provide, for example, the auxiliary sensor data 116 to the condition detection component 102. In one embodiment, the one or more auxiliary sensors 506 can be one or more sensors external from the virtual reality device. In one example, the one or more auxiliary sensors 506 can be one or more cameras, one or more microphones and/or one or more other sensors external from the virtual reality device. For instance, the one or more auxiliary sensors 506 can generate optical data indicative of optical information associated with the virtual reality device. Additionally or alternatively, the one or more auxiliary sensors 506 can generate auditory data indicative of auditory information associated with the virtual reality device. In another embodiment, the one or more auxiliary sensors 506 can be one or more sensors external from the computing device associated with augmented reality. In one example, the one or more auxiliary sensors 506 can be one or more cameras, one or more microphones and/or one or more other sensors external from the computing device associated with augmented reality. For instance, the one or more auxiliary sensors 506 can generate optical data indicative of optical information associated with the computing device associated with augmented reality. Additionally or alternatively, the one or more auxiliary sensors 506 can generate auditory data indicative of auditory information associated with the computing device associated with augmented reality.

Figure 6:
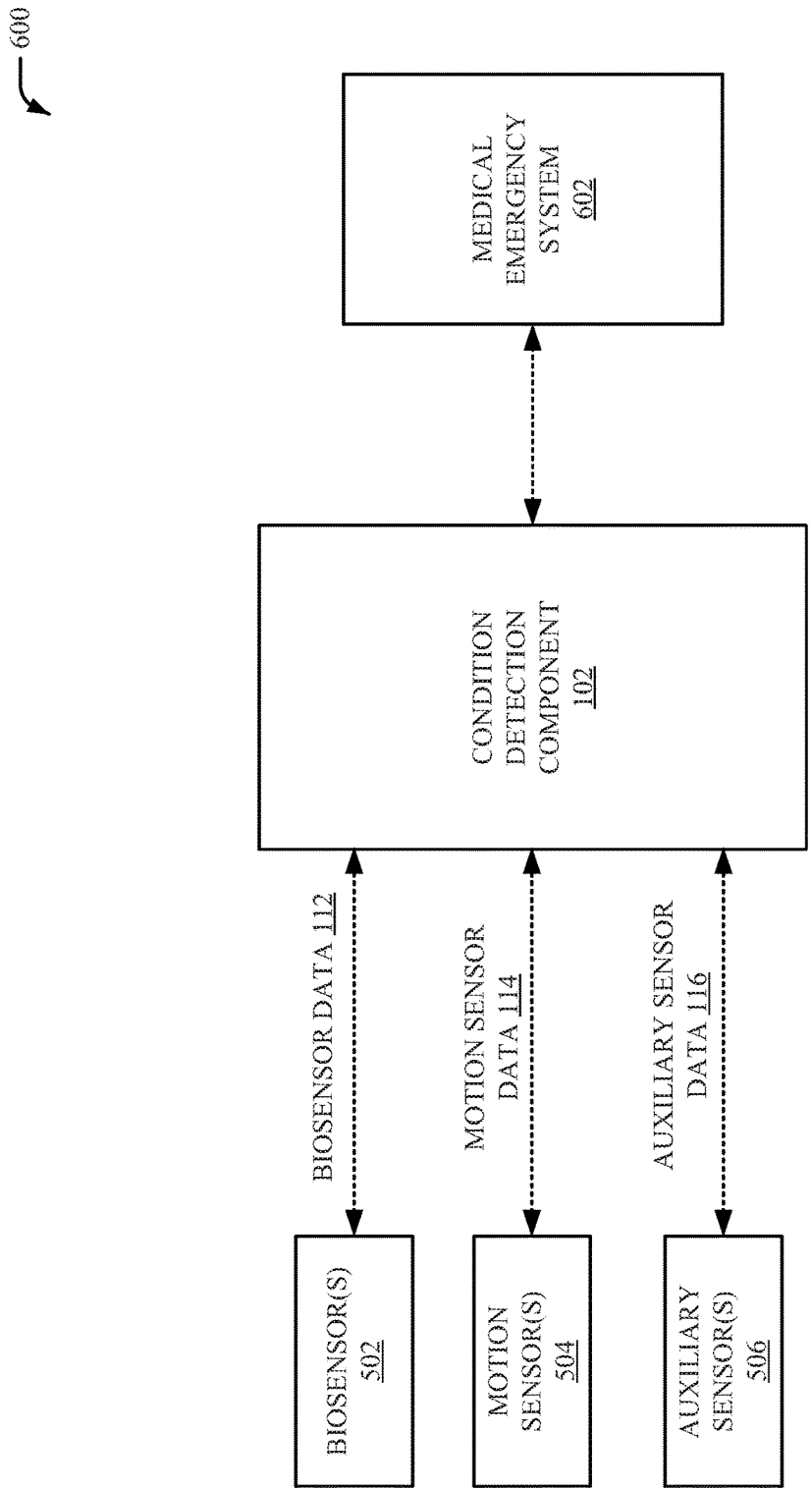
FIG. 6 illustrates an example, non-limiting system that includes a condition detection component and a medical emergency system in accordance with one or more embodiments described herein.

FIG. 6 illustrates a block diagram of an example, non-limiting system 600 in accordance with one or more embodiments described herein. Repetitive description of like elements employed in other embodiments described herein is omitted for sake of brevity.

The system 600 includes the one or more biosensors 502, the one or more motion sensors 504 and/or the one or more auxiliary sensors 506. The system 600 additionally or alternatively includes the condition detection component 102 and/or a medical emergency system 602. The condition detection component 102 can include the virtual reality component 104, the anomaly detection component 106, the memory 108, the processor 110, the machine learning component 202 and/or the condition confirmation component 302. In an embodiment, the condition detection component 102 can generate the anomaly detection data 118 based on the biosensor data 112, the motion sensor data 114 and/or the auxiliary sensor data 116, as more fully disclosed herein. Furthermore, in response to a determination that the anomaly detection data 118 satisfies a defined criterion, the condition detection component 102 can present a message on a graphical user interface for a virtual reality device and/or a computing device associated with the biosensor data 112, the motion sensor data 114 and/or the auxiliary sensor data 116. For example, in response to a determination that the anomaly detection data 118 is associated with a condition for the user (e.g., the anomaly detection data 118 detects a fall of a user associated with the biosensor data 112, the motion sensor data 114 and/or the auxiliary sensor data 116), the condition detection component 102 can present a message on a graphical user interface for a virtual reality device and/or a computing device associated with the biosensor data 112, the motion sensor data 114 and/or the auxiliary sensor data 116. The message can, for example, ask the user to confirm that no medical attention is needed. In response to a determination that the message satisfies a defined criterion, the condition detection component 102 can transmit a message to the medical emergency system 602. For example, in response to a determination that no response is provided via the graphical user interface during a defined period of time that the message is displayed, the condition detection component 102 can transmit a message to the medical emergency system 602. In another example, in response to a determination that the user confirms the condition (e.g., the fall) via the graphical user interface, the condition detection component 102 can transmit a message to the medical emergency system 602. The medical emergency system 602 can be, for example, a system for handling a medical emergency. For example, the medical emergency system 602 can call a predefined emergency contact associated with the virtual reality device and/or the computing device. In another example, the medical emergency system 602 can call an emergency service number and can provide a previously generated emergency message for the virtual reality device and/or the computing device. In certain embodiments, the medical emergency system 602 can be a medical emergency device configured to process one or more emergency requests.

Figure 7:
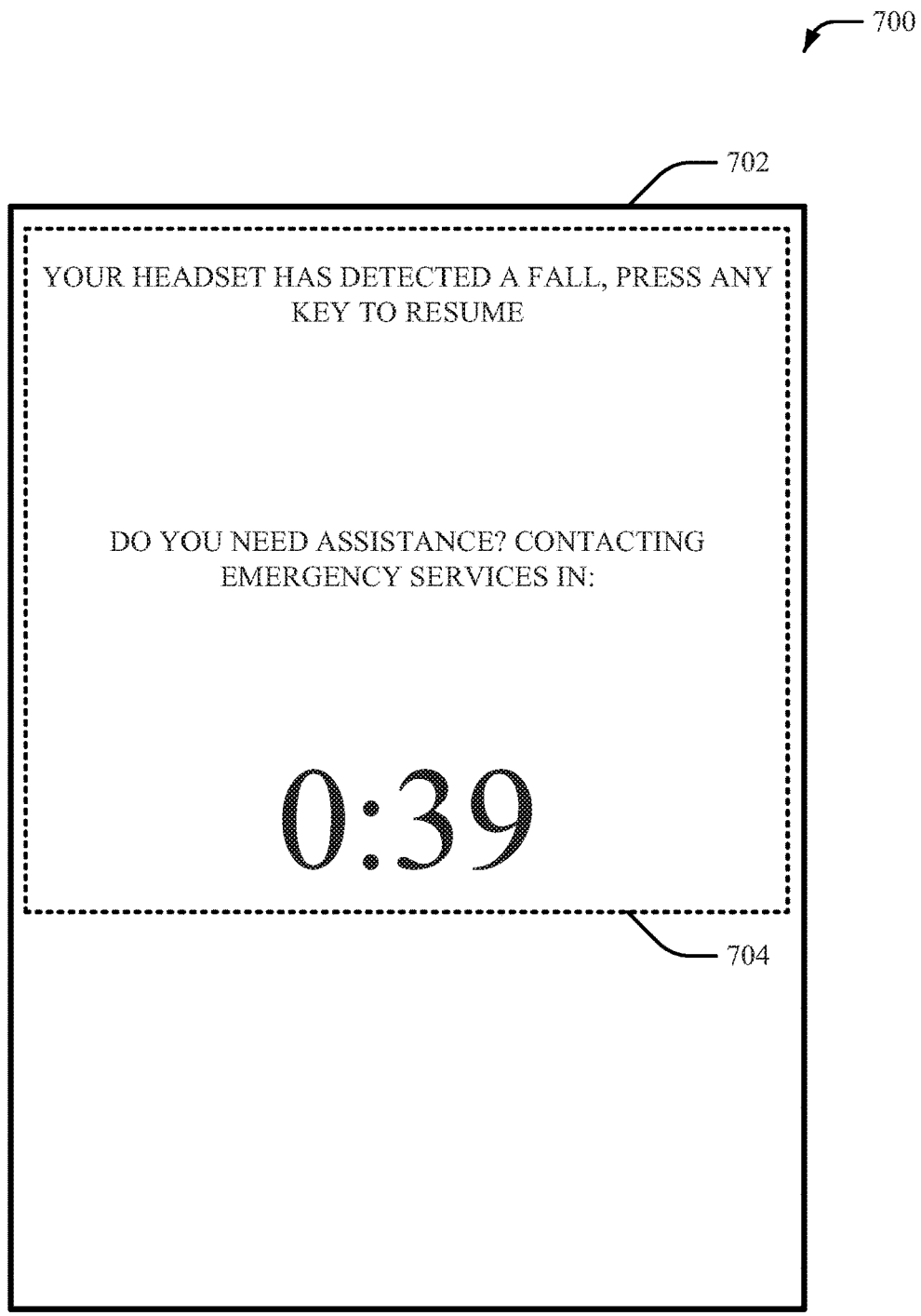
FIG. 7 illustrates an example, non-limiting graphical user interface in accordance with one or more embodiments described herein.

Referring to FIG. 7, there is illustrated a non-limiting implementation of a system 700, in accordance with various aspects and implementations of this disclosure. Repetitive description of like elements employed in other embodiments described herein is omitted for sake of brevity.

The system 700 illustrates an example graphical user interface 702. In an embodiment, the graphical user interface 702 can be presented on a display of a virtual reality device. In another embodiment, the graphical user interface 702 can be presented on a display of a computing device associated with augmented reality (e.g., an augmented reality device). For example, the graphical user interface 702 can be presented on a display of a smart phone, a mobile device, a handheld device, a tablet, a wearable device, a smart device, a portable computing device, a computer, a desktop computer, a laptop computer, a monitor device, or another type of device associated with a display to facilitate augmented reality. In an aspect, the graphical user interface 702 can include a message 704. The message 704 can be prompt that includes information to confirm whether a condition is associated with a user (e.g., a user identity) for a virtual reality device and/or a computing device associated with augmented reality. For example, the message 704 can include textual data such as "Your headset has detected a fall, press any key to resume" and/or "Do you need assistance? Contacting emergency services in 0:39." In certain embodiments, the message 704 can include a timer that indicates an amount of time until a medical emergency system is contacted. In a non-limiting example, a user can fall over while playing a virtual reality game on a virtual reality device. The user can be dazed, but not injured or concussed. The condition detection component 102 can detect the fall of the user, the condition detection component 102 can pause the virtual reality game, and the condition detection component 102 can prompt the user to confirm that the user does not need assistance via the message 704 associated with the graphical user interface 702. In response to a determination that the user responds to the message 704, the medical emergency system is not contacted. However, in response to a determination that the user does not respond to the message 704 before the timer has ended, the medical emergency system can be contacted. It is to be appreciated that the graphical user interface 702 is merely an example. Therefore, the location of sections associated with the graphical user interface 702 and/or content of the graphical user interface 702 can be varied. Furthermore, the graphical user interface 702 can include other features, content and/or functionalities not shown in FIG. 7.

Figure 8:
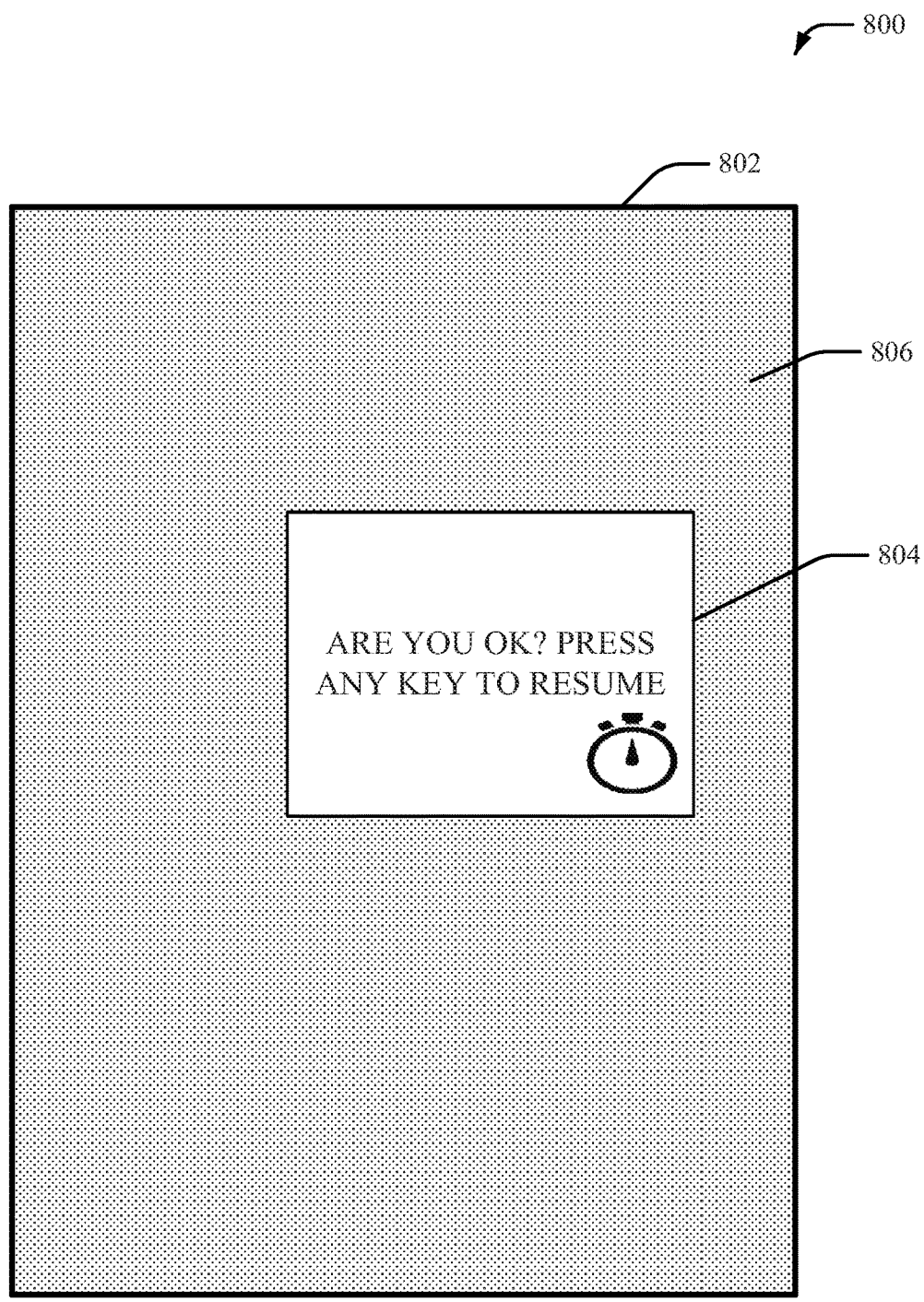
FIG. 8 illustrates another example, non-limiting graphical user interface in accordance with one or more embodiments described herein.

Referring to FIG. 8, there is illustrated a non-limiting implementation of a system 800, in accordance with various aspects and implementations of this disclosure. Repetitive description of like elements employed in other embodiments described herein is omitted for sake of brevity.

The system 800 illustrates an example graphical user interface 802. In an embodiment, the graphical user interface 802 can be presented on a display of a virtual reality device. In another embodiment, the graphical user interface 802 can be presented on a display of a computing device associated with augmented reality (e.g., an augmented reality device). For example, the graphical user interface 802 can be presented on a display of a smart phone, a mobile device, a handheld device, a tablet, a wearable device, a smart device, a portable computing device, a computer, a desktop computer, a laptop computer, a monitor device, or another type of device associated with a display to facilitate augmented reality. In an aspect, the graphical user interface 802 can include a message 804. The message 804 can be prompt that includes information to confirm whether a condition is associated with a user (e.g., a user identity) for a virtual reality device and/or a computing device associated with augmented reality. For example, the message 804 can include textual data such as "Are you ok? Press any key to resume." In certain embodiments, the message 804 can include a timer that indicates an amount of time until a medical emergency system is contacted. In another aspect, the graphical user interface 802 can include an environment 806. In one embodiment, the environment 806 can be a virtual reality environment. In another embodiment, the environment 806 can be an augmented reality environment. For example, the environment 806 can be a real-world environment with one or more augmented reality elements within the real-world environment. In a non-limiting example, a user can be playing an augmented reality game and can run into an object resulting in the user becoming unconscious. The condition detection component 102 can detect that the user has fallen, the condition detection component 102 can pause the augmented reality game, and the condition detection component 102 can prompt the user to confirm that the user does not need assistance via the message 804 associated with the graphical user interface 802. In response to a determination that the user responds to the message 804, the medical emergency system is not contacted. However, in response to a determination that the user does not respond to the message 804 before the timer has ended, the medical emergency system can be contacted.

It is to be appreciated that the graphical user interface 802 is merely an example. Therefore, the location of sections associated with the graphical user interface 802 and/or content of the graphical user interface 802 can be varied. Furthermore, the graphical user interface 802 can include other features, content and/or functionalities not shown in FIG. 8.

Figure 9:
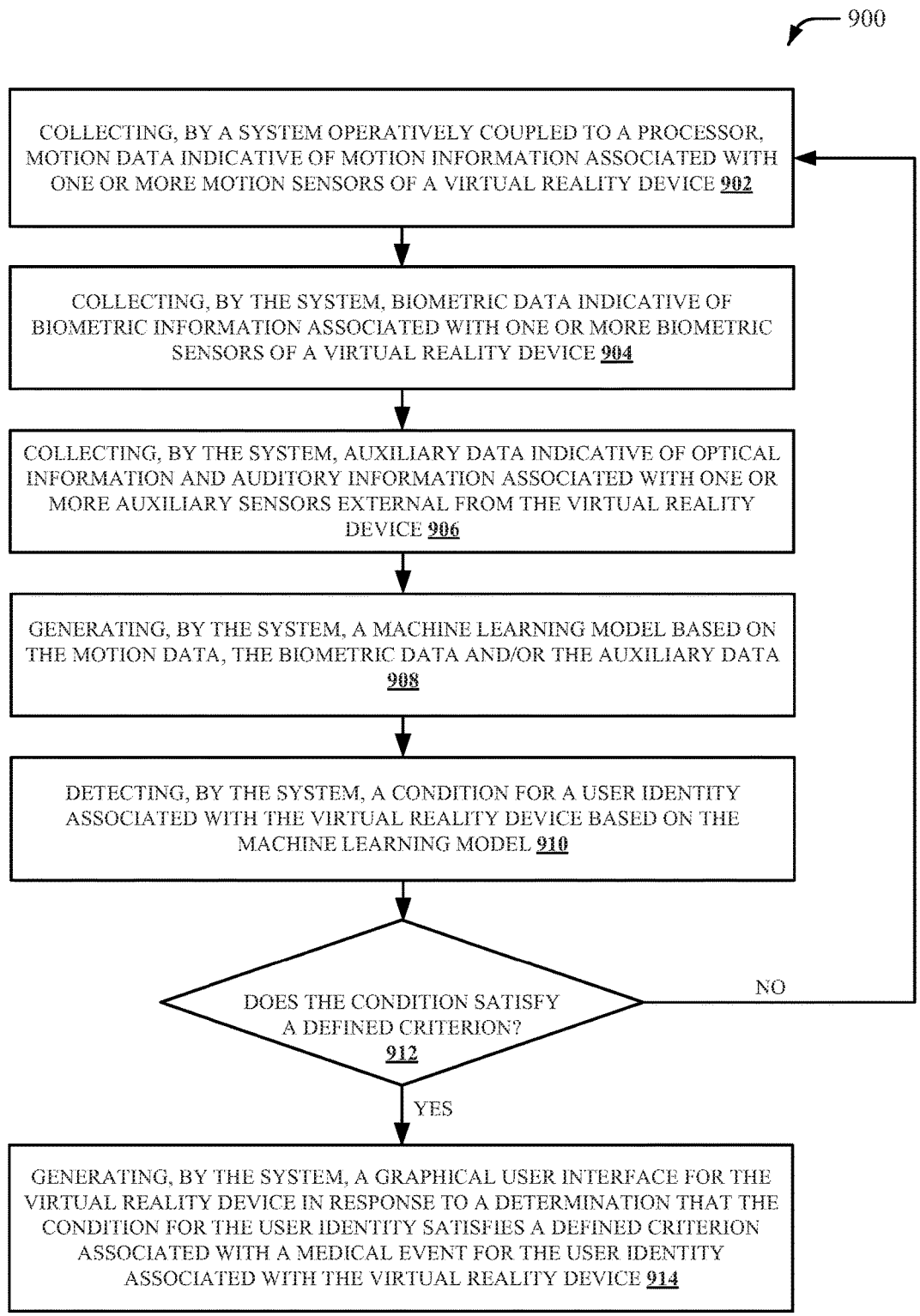
FIG. 9 illustrates a flow diagram of an example, non-limiting computer-implemented method for facilitating condition detection in a virtual reality system and/or an augmented reality system in accordance with one or more embodiments described herein.

FIG. 9 illustrates a flow diagram of an example, non-limiting computer-implemented method 900 for facilitating condition detection in a virtual reality system and/or an augmented reality system in accordance with one or more embodiments described herein. At 902, motion data indicative of motion information associated with one or more motion sensors of a virtual reality device is collected, by a system operatively coupled to a processor (e.g., by virtual reality component 104). The motion data can be motion sensor data received from one or more motion sensors. In one example, the one or more motion sensors can include one or more rotational sensors. For instance, the motion data can be rotational data received from one or more rotational sensors. Additionally or alternatively, the one or more motion sensors can include one or more positional sensors. For instance, the motion data can be positional data received from one or more positional sensors. In certain embodiments, the one or more motion sensors can be one or more accelerometers and/or one or more gyroscopes. For example, the motion data can include rotational data indicative of rotational information associated with one or more accelerometer sensors and/or positional data indicative of positional information associated with one or more positional sensors. In one embodiment, the one or more motion sensors can be one or more motion sensors of the virtual reality device. In another embodiment, the one or more motion sensors can be one or more motion sensors of a motion controller. The virtual reality device can provide a virtual reality environment to a user that employs the virtual reality deice. In one example, the virtual reality device can be a virtual reality headset (e.g., a head-mounted device) with a display that provides a virtual reality environment to a user that wears the virtual reality headset. In an alternate embodiment, the one or more motion sensors can be one or more motion sensors of a computing device associated with augmented reality. The computing device can be a smart phone, a mobile device, a handheld device, a tablet, a wearable device, a smart device, a portable computing device, a computer, a desktop computer, a laptop computer, a monitor device, or another type of device with a display associated with augmented reality. In an aspect, the computing device can render a real-world environment on a display of the computing device and the computing device can insert one or more augmented elements that are computer-generated into the real-world environment to generate an augmented reality environment.

At 904, biometric data indicative of biometric information associated with one or more biometric sensors of a virtual reality device is collected, by the system (e.g., by virtual reality component 104). The biosensor data can be biometric sensor data received from one or more biosensors. Furthermore, the one or more biosensors can record bio-activity associated with a virtual reality system and/or an augmented reality system. In certain embodiments, the one or more biosensors can be one or more electrocardiography sensors that obtain electrical activity of a biological heart during a period of time. For instance, the biosensor data can be obtained from one or more electrocardiography sensors. In another embodiment, the one or more biosensors can be one or more heart rate sensors that obtain a heart rate of a user associated with the virtual reality system and/or the augmented reality system.

At 906, auxiliary data indicative of optical information and auditory information associated with one or more auxiliary sensors external from the virtual reality device is collected, by the system (e.g., by virtual reality component 104). The auxiliary data can be auxiliary sensor data received from one or more auxiliary sensors. In one embodiment, the one or more auxiliary sensors can be one or more sensors external from the virtual reality device. In one example, the one or more auxiliary sensors can be one or more cameras, one or more microphones and/or one or more other sensors external from the virtual reality device. For instance, the auxiliary data can include optical data indicative of optical information associated with one or more auxiliary sensors external from the virtual reality device (e.g., one or more cameras, one or more microphones and/or one or more other sensors external from the virtual reality device). Additionally or alternatively, the auxiliary data can include auditory data indicative of auditory information associated with one or more auxiliary sensors external from the virtual reality device (e.g., one or more cameras, one or more microphones and/or one or more other sensors external from the virtual reality device). In another embodiment, the one or more auxiliary sensors can be one or more sensors external from the computing device associated with augmented reality. In one example, the one or more auxiliary sensors can be one or more cameras, one or more microphones and/or one or more other sensors external from the computing device associated with augmented reality. For instance, the auxiliary data can include optical data indicative of optical information associated with one or more auxiliary sensors external from the computing device associated with augmented reality (e.g., one or more cameras, one or more microphones and/or one or more other sensors external from the computing device associated with augmented reality). Additionally or alternatively, the auxiliary data can include auditory data indicative of auditory information associated with one or more auxiliary sensors external from the computing device associated with augmented reality (e.g., one or more cameras, one or more microphones and/or one or more other sensors external from the computing device associated with augmented reality).

At 908, a machine learning model is generated, by the system (e.g., by anomaly detection component 106) based on the motion data, the biometric data and/or the auxiliary data. For instance, the machine learning model can determine whether a classifiable pattern is associated with the motion data, the biometric data and/or the auxiliary data to determine whether a condition for a user of a virtual reality device and/or a computing device associated with augmented reality exists. For example, the machine learning model can detect rapid deceleration of a virtual reality device and/or a computing device associated with augmented reality based on the motion data, the biometric data and/or the auxiliary data. In another example, the machine learning model can detect rapid deceleration of a motion controller associated with the virtual reality device and/or a computing device associated with augmented reality based on the motion data, the biometric data and/or the auxiliary data. In yet another example, the machine learning model can detect a slower heartrate of a user and a slower breathing rate of the user after a fall based on the motion data, the biometric data and/or the auxiliary data. In an aspect, the machine learning model can be a classifier that provides a confidence score for a condition (e.g., a fall condition) associated with a user associated with the virtual reality device and/or a computing device associated with augmented reality. In certain embodiments, the machine learning model can be associated with a shallow classifier such as, for example, a support vector machine, a random forest, etc. In certain embodiments, the machine learning model can be associated with a deep neural network. However, it is to be appreciated that the machine learning model can be associated with another type of machine learning technique and/or another type of artificial intelligence technique.

At 910, a condition for a user identity associated with the virtual reality device is detected, by the system (e.g., by anomaly detection component 106), based on the machine learning model. For example, a medical condition for the user identity associated with the virtual reality device can be detected based on the machine learning model. Alternatively, a medical condition for the user identity associated with the computing device can be detected based on the machine learning model. In another example, a fall condition (e.g., detection of a fall) for the user identity associated with the virtual reality device (e.g., a potential injury status for the user identity associated with the virtual reality device) can be detected based on the machine learning model. Alternatively, a fall condition for the user identity associated with the computing device (e.g., a potential injury status for the user identity associated with the computing device) can be detected based on the machine learning model.

At 912, it is determined whether the condition satisfies a defined criterion. If no, the computer-implemented method 900 can return to 902. If yes, the computer-implemented method 900 can proceed to 914.

At 914, a graphical user interface for the virtual reality device is generated, by the system (e.g., by anomaly detection component 106), in response to a determination that the condition for the user identity satisfies a defined criterion associated with a medical event for the user identity associated with the virtual reality device. For example, a message for a graphical user interface associated with the virtual reality device can be generated in response to a determination that the condition for the user identity satisfies a defined criterion associated with a medical event for the user identity associated with the virtual reality device. The message can facilitate confirmation of the medical condition based on user feedback provided via the graphical user interface. In an alternate embodiment, a message for a graphical user interface associated with the computing device associated with augmented reality can be generated in response to a determination that the condition for the user identity satisfies a defined criterion associated with a medical event for the user identity associated with the computing device associated with augmented reality.

For simplicity of explanation, the computer-implemented methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts can be required to implement the computer-implemented methodologies in accordance with the disclosed subject matter. In addition, those skilled in the art will understand and appreciate that the computer-implemented methodologies could alternatively be represented as a series of interrelated states via a state diagram or events. Additionally, it should be further appreciated that the computer-implemented methodologies disclosed hereinafter and throughout this specification are capable of being stored on an article of manufacture to facilitate transporting and transferring such computer-implemented methodologies to computers. The term article of manufacture, as used herein, is intended to encompass a computer program accessible from any computer-readable device or storage media.

Moreover, because at least generating a machine learning model, detecting a condition for a user identity associated with a virtual reality device and/or a computing device associated with augmented reality, generating a graphical user interface for a virtual reality device and/or a computing device associated with augmented reality, etc. are established from a combination of electrical and mechanical components and circuitry, a human is unable to replicate or perform a condition detection process associated with the condition detection component 102 (e.g., the virtual reality component 104, the anomaly detection component 106, the machine learning component 202, and/or the condition confirmation component 302) disclosed herein. For example, a human is unable to perform a condition detection process, generate anomaly detection data (e.g., anomaly detection data 118), etc.

Figure 10:
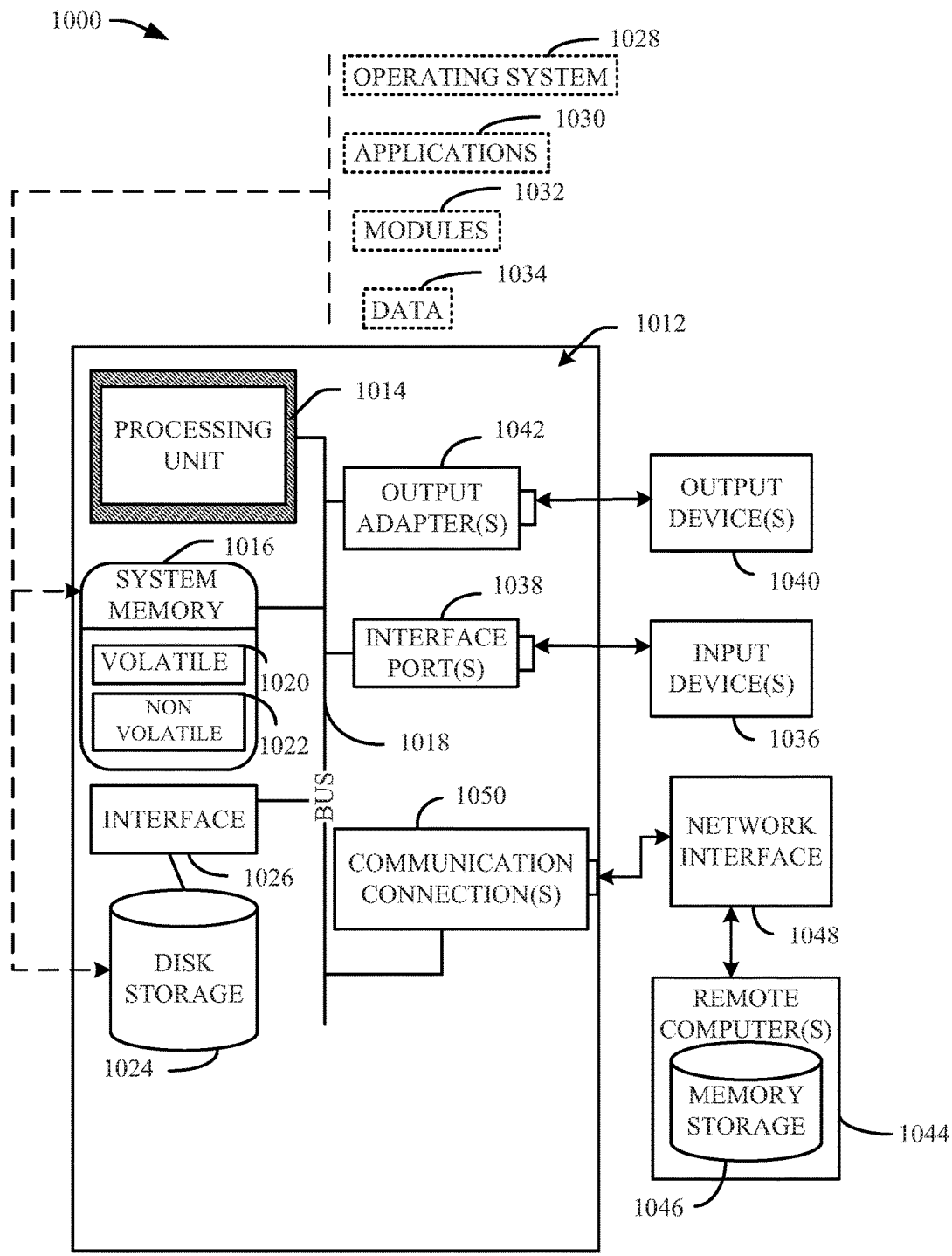
FIG. 10 illustrates a block diagram of an example, non-limiting operating environment in which one or more embodiments described herein can be facilitated.

In order to provide a context for the various aspects of the disclosed subject matter, FIG. 10 as well as the following discussion are intended to provide a general description of a suitable environment in which the various aspects of the disclosed subject matter can be implemented. FIG. 10 illustrates a block diagram of an example, non-limiting operating environment in which one or more embodiments described herein can be facilitated. Repetitive description of like elements employed in other embodiments described herein is omitted for sake of brevity.

With reference to FIG. 10, a suitable operating environment 1000 for implementing various aspects of this disclosure can also include a computer 1012. The computer 1012 can also include a processing unit 1014, a system memory 1016, and a system bus 1018. The system bus 1018 couples system components including, but not limited to, the system memory 1016 to the processing unit 1014. The processing unit 1014 can be any of various available processors. Dual microprocessors and other multiprocessor architectures also can be employed as the processing unit 1014. The system bus 1018 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI).

The system memory 1016 can also include volatile memory 1020 and nonvolatile memory 1022. The basic input/output system (BIOS), containing the basic routines to transfer information between elements within the computer 1012, such as during start-up, is stored in nonvolatile memory 1022. Computer 1012 can also include removable/non-removable, volatile/non-volatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media. To facilitate connection of the disk storage 1024 to the system bus 1018, a removable or non-removable interface is typically used, such as interface 1026. FIG. 10 also depicts software that acts as an intermediary between users and the basic computer resources described in the suitable operating environment 1000. Such software can also include, for example, an operating system 1028. Operating system 1028, which can be stored on disk storage 1024, acts to control and allocate resources of the computer 1012.

System applications 1030 take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems. A user enters commands or information into the computer 1012 through input device(s) 1036. Input devices 1036 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1014 through the system bus 1018 via interface port(s) 1038. Interface port(s) 1038 include, for example, a serial port, a parallel port, a game port, and a universal serial bus (USB). Output device(s) 1040 use some of the same type of ports as input device(s) 1036. Thus, for example, a USB port can be used to provide input to computer 1012, and to output information from computer 1012 to an output device 1040. Output adapter 1042 is provided to illustrate that there are some output devices 1040 like monitors, speakers, and printers, among other output devices 1040, which require special adapters. The output adapters 1042 include, by way of illustration and not limitation, video and sound cards that provide a means of connection between the output device 1040 and the system bus 1018. It should be noted that other devices and/or systems of devices provide both input and output capabilities such as remote computer(s) 1044.

Computer 1012 can operate in a networked environment using logical connections to one or more remote computers, such as remote computer(s) 1044. The remote computer(s) 1044 can be a computer, a server, a router, a network PC, a workstation, a microprocessor based appliance, a peer device or other common network node and the like, and typically can also include many or all of the elements described relative to computer 1012. For purposes of brevity, only a memory storage device 1046 is illustrated with remote computer(s) 1044. Remote computer(s) 1044 is logically connected to computer 1012 through a network interface 1048 and then physically connected via communication connection 1050. Network interface 1048 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM).

Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has,"

"possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
    a memory that stores computer executable components;
    a processor that executes computer executable components stored in the memory, wherein the computer executable components comprise:
        a virtual reality component that collects motion data and biometric data from a virtual reality device, wherein the motion data is indicative of motion information associated with one or more accelerometer sensors of the virtual reality device, wherein the motion data is indicative of rotational information associated with the one or more accelerometer sensors and positional information associated with one or more positional sensors of the virtual reality device, and wherein the biometric data is indicative of biometric information associated with one or more biometric sensors of the virtual reality device; and
        an anomaly detection component that integrates the motion data and the biometric data into a machine learning model to generate anomaly detection data for the virtual reality device.

2. The system of claim 1, wherein the anomaly detection component determines whether the anomaly detection data satisfies a defined criterion associated with a medical event for a user identity associated with the virtual reality device.

3. The system of claim 1, wherein the anomaly detection component determines whether the anomaly detection data satisfies a defined criterion associated with a concussion medical status for a user identity associated with the virtual reality device.

4. The system of claim 1, wherein the anomaly detection component determines a period of unconsciousness for a user identity associated with the virtual reality device based on the anomaly detection data.

5. The system of claim 1, wherein the anomaly detection component transmits a message to a medical emergency device in response to a determination that the anomaly detection data satisfies a defined criterion associated with a medical event for a user identity associated with the virtual reality device.

6. The system of claim 1, wherein the anomaly detection component generates a graphical user interface for the virtual reality device in response to a determination that the anomaly detection data satisfies a defined criterion associated with a medical event for a user identity associated with the virtual reality device.

7. The system of claim 6, wherein the defined criterion is a first defined criterion, and wherein the anomaly detection component transmits a message to a medical emergency device in response to a determination that the graphical user interface satisfies a second defined criterion associated with the user identity.

8. The system of claim 1, wherein the virtual reality component collects auxiliary data from the virtual reality device, and wherein the auxiliary data is indicative of optical information and auditory information associated with one or more auxiliary sensors external from the virtual reality device.

9. The system of claim 8, wherein anomaly detection component integrates the auxiliary data, the motion data, and the biometric data into the machine learning model.

10. The system of claim 1, wherein the anomaly detection component generates the anomaly detection data for the virtual reality device to facilitate reduced likelihood of a medical condition for a user identity associated with the virtual reality device.

11. A computer-implemented method, comprising:
    collecting, by a system operatively coupled to a processor, motion data indicative of motion information associated with one or more motion sensors of a virtual reality device, wherein the collecting the motion data comprises collecting rotational data associated with the one or more motion sensors and positional data associated with one or more positional sensors of the virtual reality device;
    collecting, by the system, biometric data indicative of biometric information associated with one or more biometric sensors of a virtual reality device; and
    generating, by the system, a machine learning model based on the motion data and the biometric data; and
    detecting, by the system, a condition for a user identity associated with the virtual reality device based on the machine learning model.

12. The method of claim 11, further comprising:
    determining, by the system, whether the condition for the user identity satisfies a defined criterion associated with a medical event for the user identity associated with the virtual reality device.

13. The method of claim 11, further comprising:
    generating, by the system, a graphical user interface for the virtual reality device in response to a determination that the condition for the user identity satisfies a defined criterion associated with a medical event for the user identity associated with the virtual reality device.

14. The method of claim 11, further comprising:
    collecting, by the system, auxiliary data indicative of optical information and auditory information associated with one or more auxiliary sensors external from the virtual reality device, and wherein the generating the machine learning model comprises generating the machine learning model based on the auxiliary data, the motion data, and the biometric data.

15. The method of claim 11, wherein the detecting the condition comprises detecting the condition to facilitate reduced likelihood of a medical condition for the user identity associated with the virtual reality device.

16. A computer program product facilitating fall detection associated with virtual reality, the computer program product comprising a computer readable storage medium having program instructions embodied therewith, the program instructions executable by a processor to cause the processor to:
    obtain, by the processor, motion data indicative of motion information associated with one or more accelerometer sensors of a virtual reality device;

obtain, by the processor, biometric data indicative of biometric information associated with one or more biometric sensors of a virtual reality device;

generate, by the processor, a machine learning model based on the motion data and the biometric data;

detect, by the processor, a condition for a user identity associated with the virtual reality device based on the machine learning model; and generate, by the processor, a graphical user interface for the virtual reality device in response to a determination that the condition for the user identity satisfies a defined criterion associated with a medical event for the user identity associated with the virtual reality device.

17. The computer program product of claim 16, wherein the program instructions are further executable by the processor to cause the processor to:

obtain, by the processor, auxiliary data indicative of optical information and auditory information associated with one or more auxiliary sensors external from the virtual reality device; and generate, by the processor, the machine learning model based on the auxiliary data, the motion data, and the biometric data.

\* \* \* \* \*